(12) United States Patent
Heinrichs (10) Patent No.: US 6,265,393 B1
(45) Date of Patent: *Jul. 24, 2001

(54) PREVENTION OF ENDOMETRIOSIS SIGNS OR SYMPTONS

(76) Inventor: William LeRoy Heinrichs, 8 Campbell La., Menlo Park, CA (US) 94025

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/130,880

(22) Filed: Aug. 7, 1998

(51) Int. Cl.$^7$ ...................................................... A61P 15/08

(52) U.S. Cl. .......................... 514/178; 514/178; 514/182; 514/800; 514/171; 514/899

(58) Field of Search ............................................. 514/170

(56) References Cited

U.S. PATENT DOCUMENTS

| 4,906,169 | 3/1990 | Chien ................................... | 424/448 |
|---|---|---|---|
| 5,340,585 | 8/1994 | Pike ..................................... | 424/426 |
| 5,552,394 | 9/1996 | Hodgen ................................ | 514/178 |
| 5,554,600 | 9/1996 | Fontana ................................ | 514/182 |
| 5,591,753 | 1/1997 | Black ................................... | 514/324 |
| 5,618,817 | 4/1997 | Björk ................................... | 514/255 |
| 5,646,137 | 7/1997 | Black et al. .......................... | 514/171 |
| 5,658,884 | 8/1997 | Hodgen ................................ | 514/12 |

OTHER PUBLICATIONS

ACOG Committee, "Medical Management of Endometriosis," *AGOC Practice Bulletin: Clinical Management Guidelines for Obstetrician–Gynecologists*, No. 11, pp. 1–14, Dec. 1999.

Alger, "The Danger Within," *Forbes*, pp. 338–341, Dec. 13, 1999.

Metzger, "Treating Endometriosis Pain: A Multidisciplinary Approach," *Seminars in Reproductive Endocrinology*, 15(3):245–250, 1997.

Agarwal, Nafarelin vs. Leuprolide Acetate Depot for Endometriosis: Changes in Bone Mineral Density and Vasomotor Symptoms, *J. Reprod. Med.*, vol. 42, pp. 413–423, (1997).

Newhall–Perry, Effects of a GnRH Agonist on the Calcium–Parathyroid Axis and Bone Turnover in Women with Endometriosis, *Am. J. Obstet. And Gynecol.*, vol. 173, pp. 824–829, (1995).

Barbieri, Hormone Treatment of Endometriosis: The Estrogen Threshold Hypothesis, *Am. J. Obstet. Gynecol.*, vol. 166, pp. 740–745, (1992).

Eldred, A Randomized, Double Blind, Placebo Controlled Trial of the Effects on Bone Metabolism of the Combination of Nafarelin Acetate and Norethisterone, *Cline. Endocrinol.*, (Oxford), vol. 37, pp. 354–359, (1992).

Hornstein, Retreatment with Nafarelin for Recurrent Endometriosis Symptoms: Efficacy, Safety and Bone Mineral Density, *Fertility and Sterility*, vol. 67, pp. 1013–1018, (1997).

Shaw, An Open Randomized Comparative Study of the Effect of Goserelin Depot and Danazol in the Treatment of Endometriosis, *Fertility and Sterility*, vol. 58, pp. 265–272, (1992).

(List continued on next page.)

*Primary Examiner*—Edward J. Webman
(74) *Attorney, Agent, or Firm*—Cooley Godward LLP (57) ABSTRACT

Methods and articles of manufacture are provided for the long-term prevention of clinical symptoms and signs produced by endometriosis. Such methods and articles of manufacture involve the continuous coadministration of low doses of an estrogen agent and a progestin agent to maintain an induced state of oligomenorrhea or amenorrhea in an afflicted woman.

22 Claims, 2 Drawing Sheets

OTHER PUBLICATIONS

Sutton, Prospective, Randomized, Double–Blind, Controlled Trial of Laser Laparoscopy in the Treatment of Pelvic Pain Associated with Minimal, Mild and Moderate Endometriosis, *Fertility and Sterility*, vol. 62, pp. 696–700, (1994).

Palter, Office Microlaparoscopy Under Local Anesthesia for Chronic Pelvic Pain, *J. Am. Assoc. Gynecol. Laparos.*, vol. 3, pp. 359–364, (1996).

Feber, Microlaparoscopy: A Comparative Study of Diagnostic Accuracy, *Fertility and Sterility*, vol. 67, pp. 952–954, (1997).

Fishburne, Office Laparoscopic Sterilization with Local Anesthesia, *J. Reprod. Med.*, vol. 18, pp. 233–234, (1977).

Casey, Laparoscopy Under Local Anesthesia, *J. R. Soc. Med.*, vol. 77, pp. 985–986, (1984).

Milki, Office Laparoscopy Under Local Anesthesia for Gamete Intrafallopian Transfer: Technique and Tolerance, *Fertility and Sterility*, vol. 68, pp. 128–132, (1997).

Candiani, Repetitive Conservative Surgery for Recurrence of Endometriosis, *Obstet. Gynecol.*, vol. 77, pp. 421–424, (1991).

Pasquale, Clinical Results with a New Low–Dose Oral Contraceptive Utilizing Norethindrone/Ethinyl Estradiol, *Contraception*, vol. 12, pp. 495–503, (1975).

Bounds, A Randomized Double–Blind Trial of Two Low Dose Combined Oral Contraceptives, *Br. J. Obstet. Gynecol*, vol. 86, 325–329, (1979).

Williams, A Study of Combined Continuous Ethinyl Estradiol and Norethindrone Acetate for Postmenopausal Hormone Replacement, *Am. J. Obstet. Gynecol.*, vol. 162, pp. 438–446, (1990).

Hawkins, A Comparative Study of Three Low Dose Progestogens, Chlormadinone Acetate, Megestrol Acetate and Norethisterone, As Oral Contraceptives, *Br. J. Obstet. Gynecol.*, vol. 84, pp. 703–713, (1977).

Stadberg, β–Estradiol and Noretheisterone Acetate in Low Doses as Continuous Combined Hormone Replacement Therapy, *Maturitas*, vol. 23, pp. 31–39, (1996).

Plunkett, Prolonged Effects of a Novel, Low–Dosage Continuous Progestin–Cyclic Estrogen Replacement Program in Postmenopausal Women, *Am. J. Obstet. And Gynecol.*, vol. 166, pp. 117–121, (1992).

The Writing Group for the Pepi Trial, Effects of Estrogen or Estrogen/Progestin Regimens on Heart Disease Risk Factors in Postmenopausal Women, *JAMA*, vol. 273, pp. 199–208, (1996).

Johannisson, Transdermal Sequential and Continuous Hormone Replacement Regimens with Estradiol and Norethisterone Acetate in Postmenopausal Women: Effects on the Endometrium, *Int. J. Fertil. Womens Med.*, vol. 42 Suppl. 2, pp. 388–398, (1997).

Rozenberg, Comparison of Continuous and Sequential Transdermal Progestogen with Sequential Oral Progestogen in Postmenopausal Women Using Continuous Transdermal Estrogen: Vasomotor Symptoms, Bleeding Patterns, and Serum Lipids, *Int. J. Fertil. Womens Med.*, vol. 42 Suppl. 2, pp. 376–387, (1997).

Sitruk–Ware, Transdermal Application of Steroid Hormones for Contraception, *J. Steroid. Biochem. Mol. Bio.*, vol. 53(1–6), pp. 247–251, (1995).

Oosterbaan, The Effects of Continuous Combined Transdermal Oestrogen–Progestogen Treatment on Bleeding Patterns and the Endometrium in Postmenopausal Women, *Maturitas*, vol. 21(3), pp. 211–219, (1995).

Wright, Short–Term Lupron and Danazol Therapy for Pelvic Endometriosis, *Fertility and Sterility*, vol. 63(3), pp. 504–507 (1995).

Bergqvist, A Double–Blind Randomized Study of the Treatment of Endometriosis with Nafarelin or Nararelin Plus Norethisterone, *Gynecol. Endocrinol.*, vol. 11(3), pp. 187–194, (1997).

Lindsay, The Effect of Add–Back Treatment With Tibolone (Livial) On Patients Treated With The Gonadotropin–Releasing Hormone Agonist Triptorelin (Decapeptyl), *Fertility and Sterility*, vol. 65(2), pp. 342–348, (1996).

Vercellini, Very Low Dose Danazol For Relief of Endometriosis–Associated Pelvic Pain: A Pilot Study, *Fertility and Sterility*, vol. 62(6), pp. 1136–1142, (1994).

Worthington, A Randomized Comparative Study of the Metabolic Effects of Two Regimens of Gestrinone in the Treatment of Endometriosis, *Fertility and Sterility*, vol. 59(3), pp. 522–526, (1993).

Kistner, The Use of Newer Progestins in the Treatment of Endometriosis, *Am. J. Obstet. Gynecol.*, vol. 75, pp. 265–278, (1958).

Andrews, Effects of Progestin–Induced Pseudopregnancy on Endometriosis: Clinical and Microscopic Studies, *Am. J. Obstet. Gynecol.*, vol. 78, pp. 776–785, (1959).

Metzger, Hormonal Therapy of Endometriosis, *Endometriosis*, vol. 16, pp. 105–122, (1989).

Wheeler, Combined Medical and Surgical Therapy for Endometriosis, *Current Concepts in Endometriosis*, pp. 281–288, (1990), Alan R. Liss Inc.

Henzl, Administration of Nasal Nafarelin as Compared with Oral Danazol for Endometriosis—a Multi–Center, Double–Blind, Comparative Clinical Trial, *N. Eng. J. Med*, vol. 318, pp. 485–489, (1988).

PREVENTION OF ENDOMETRIOSIS SIGNS OR SYMPTOMS

INTRODUCTION

1. Technical Field

The present invention relates to the coadministration of an estrogen agent and a progestin agent in low doses for the long-term prevention of endometriosis signs or symptoms.

2. Background

Many women, approximately 5–10 percent of those in their reproductive years, are afflicted with endometriosis and suffer progressive, disabling dysmenorrhea and pelvic pain around the time of their menses (Brosens, Endometriosis-A Disease Because it is Characterized by Bleeding, *Am. J. Obstet. Gynecol.* 176:263–7 (1997)). In addition, pelvic pain unassociated with menses may restrict afflicted women to measured participation in athletic and other physical activities, such as dancing and hiking. Through dyspareunia, they suffer not only the pain and often-missed orgasmic fulfillment, but also the doubts of sincerity and the cautious love of their sexual partners, perhaps even marital discord, separation, or infertility. Through relative infertility, they suffer further reductions in self-esteem from the pangs of guilt and failure engendered by struggles to conceive, suffering that adds personal, physical, and economic cost. Often, coital events or pelvic exams produce pelvic aching for hours or even days thereafter.

The peri-menstrual pain experienced by afflicted women may be relieved in part by non-steroidal anti-inflanmmatory drugs (NSAID's). But those not benefitted adequately require ovulation-suppressing treatments, or finally laparoscopy, where the majority are discovered to have the findings typical of endometriosis, i.e., ectopic 'implants' of endometrial tissue on the peritoneal surface of the pelvis or extra-genital areas. Others with unexplained infertility have similar findings.

The current concept of this disease is that endometrial glands and stroma are shed through Fallopian tubes during menstruation, after which they implant onto the peritoneum, and initiate growth. Initially, the existence of translocated endometrial cells can only be proven microscopically on the peritoneal lining of the pelvis, or even at extra-pelvic sites such as the diaphragm in the upper abdomen (Murphy et al., Unsuspected Endometriosis Documented by Scanning Electron Microscopy in Visually Normal Peritoneum, *Fert. and Sterility* 46: 522–524 (1986)). But the occurrence of regular, menstrual bleeding at those sites over time leads to angiogenesis and growth of visible lesions where none had been visible before, and pain and infertility that develop from the bleeding at, and into those sites (Brosens). Symptoms usually subside during pregnancy and lactation, after castration premenopausally, and as the hypoestrogenemia of the perimenopause develops. Endometriosis is a life-long, genetically facilitated, pathological condition that may be stimulated at any age by unopposed estrogen therapy to produce recurrent symptoms.

This retrograde menstruation concept as the initiator of the disease of endometriosis is consistent with clinical observations that amenorrhea, the lack of uterine bleeding (and presumed concomitant failure of the ectopic lesions to bleed), is therapeutic for endometriosis. Astute physicians first noted in the 1920's, that castration was therapeutic. In the 1930's, they recognized that pregnancy, with its gestational and lactational amenorrhea, often provided relief from cyclic pelvic pain for months thereafter, but that recurrence was frequent.

In the late 1950's, the continuous coadministration of 19-norsteroids and estrogen emerged as a medical treatment of endometriosis. Regimen of increasing doses for 3–4 months duration, or longer, were found effective for creating a "pseudopregnancy" (Kistner, The use of newer progestins in the treatment of endometriosis, *Am. J. Obstet. and Gynecol.* 75: 265–278 (1958); Andrews et al., Effects of progestin-induced pseudopregnancy on endometriosis: clinical and microscopic studies, *Am. J. Obstet. and Gynecol.* 78: 776–785 (1959)). This treatment also provided a high incidence of amenorrhea, and temporary relief thereafter, but its use was limited by the severe side-effects from the very large doses of the agents necessary to suppress the ovarian cycle and the endometrium.

Application of low-dose oral conceptives in the present invention is different from prior indications in which such agents are administered cyclically and electively to young women for contraception, or in which such agents are administered without interruption to postmenopausal women for hypoestrogenemia. While estrogen agents and progestin agents have been coadministered to reproductive age women before, such agents have been coadministered on a cyclic basis for contraception. Such agents have been coadministered continuously as a postmenopausal hormone replacement therapy, but the women receiving such therapy are past reproductive age. Studies in which a woman's response to oral contraceptives was used to diagnose or treat endometriosis suggested little benefit in the prevention of endometriosis symptoms and long-term hormonal suppression was disfavored (Metzger et al., Hormonal Therapy of Endometriosis, *Endometriosis* 16: 105–122 (1989)). Several studies suggested that added pseudopregnancy induced by high dose oral contraceptives was detrimental (Metzger et al.; Wheeler et al., Combined Medical and Surgical Therapy for Endometriosis, *Current Concepts in Endometriosis* p. 281–288, 1990 Alan R. Liss, Inc.). In all of such "pseudopregnancy" studies, oral contraceptives were administered to reproduce the symptoms and signs of endometriosis until amenorrhea was achieved. The common practice was to then discontinue treatment and observe the patient for the recurrence of symptoms. Intolerance to pseudopregnancy regimen, producing side effects such as abdominal swelling, depression, breast tenderness, increased appetite, weight gain and edema, breakthrough bleeding, nausea, breast secretion, and vein varicosity was the most common reason for discontinuation. Thus, physicians have historically been reluctant to treat endometriosis with continuous regimen of oral contraceptives. Prior to this invention, low doses of estrogen agents and progestin agents have never been coadministered continuously and prophylactically following other therapeutic regimen that produce amenorrhea, for preventing the recurrence of symptoms and signs of endometriosis in reproductive age women.

Another therapeutic approach with a synthetic, progestational androgen, danazol, has been used successfully for producing a "pseudomenopause" during a six month treatment schedule (Henzl for the Nafarelin Group, Administration of Nasal Nafarelin as Compared with Oral Danazol for Endometriosis-a Multi-Center, Double-Blind, Comparative Clinical Trial, *N. Eng. J. Med.* 318: 385–9 (1988)). This descriptive term was advanced because the drug reduced circulating estrogen levels and produced amenorrhea in the majority of treated women. The side-effects of masculinization and liver damage restricted the widespread use of danazol.

At about the same time, the oral or parenteral treatment of women with pelvic pain from endometriosis with 6-medroxy-progesterone, a widely used synthetic progestin, was found in high doses to reduce the severity of pelvic pain. Emotional depression, bloating, and weight gain resulting from the large doses necessary to achieve the relief of pain doomed these medical therapeutic approaches to disuse (Hornstein et al., A Randomized, Double-blind Trial of 3 versus 6 Months of Nafarelin Therapy for Endometriosis-associated Pelvic Pain, *Fertility and Sterility*, 63:955–62 (1995)).

The next pharmacological advance for endometriosis therapy was the synthesis and formulation of gonadotropin-releasing hormone agonists (GnRH-agonist) which act at the hypothalamus and hypophysis to suppress the gonadotropin-mediated, ovarian secretion of estrogen (Henzl et al.). The condition so induced was labeled as a "pseudo-ovariectomy". As a consequence of the resulting hypoestrogenemia, the endometrium becomes atrophic, and amenorrhea occurs promptly for 80–90 percent of treated patients. Except for rare anaphylactic responses, this therapeutic approach has been successful in producing only the symptoms of the hypoestrogenemia desired from the therapy. Initially, studies and application of GnRH-agonists for FDA approval were for six-months long treatment regimen (Henzl et al). However, recent studies indicate that three months of GnRH-a therapy is nearly as efficacious for the symptoms and signs of endometriosis as is six months (Hornstein et al). Further, the shorter regimen was associated with less severe side-effects. (Agarwal et al., Nafarelin vs. Leuprolide Acetate for Endometriosis: Changes in Bone Mineral Density and Vasomotor Symptoms, *J. Reprod. Med.* 42: 413–23 (1997)).

However, the side-effects of hypoestrogenemia include the decrease of bone mineral density, which has been of concern (Newhall-Perry et al., Effects of a GnRH Agonist on the Calcium-parathyroid Axis and Bone Turnover in Women with Endometriosis, *Am. J. Obstet. and Gynecol.*, 173: 824–9 (1995)). Therefore, the FDA has approved only one six-month course of treatment with GnRH-agonist for endometriosis (Henzl et al). Repeated courses have not been recommended for fear of permanent harm to bone structure. Unfortunately, symptoms and signs of endometriosis recur in at least 50% of patients within five years after completion of GnRH-agonist treatment (Waller et al., Gonadotropin-Releasing Hormone Analogues for the Treatment of Endometriosis: Long-term Follow-up, *Fertility and Sterility* 59:511–515 (1993); Regidor et al., Long-term Follow-up (up 98 months) of 42 Patients Treated for Endometriosis with the GnRH-agonist Buserelin Acetate: Recurrence of Pain Symptoms and Pregnancy Outcome, *Eur. J. Obstet. Gynecol. Reprod. Biol.* 73: 153–60 (1997)), and further therapy of some type becomes necessary for many women with endometriosis.

Reductions in bone mineral density led to the concept of "add-back" therapy with estrogen or selected progestins concurrently with GnRH-agonist for reducing the adverse symptoms and the risk of induced bone disease. (Barbieri, R. L., Hormone Treatment of Endometriosis: The Estrogen Threshold Hypothesis, *Am. J. Obstet. Gynecol.* 166: 740–5 (1992)). Added estrogen, although effective for reducing some of the systemic adverse effects of the agonist therapy, is associated with breakthrough bleeding in up to 40 percent of patients receiving 1.25 mg of conjugated equine estrogen, but only 15 percent when the 19-norprogestin, norethindrone, is added (Eldred et al., A Randomized, Double-Blind, Placebo-Controlled Trial of the Effects on Bone Metabolism of the Combination of Nafarelin Acetate and Norethisterone, *Clin. Endocrinol.* (Oxford), 37: 354–9 (1992)). Unfortunately, the administration of additional drugs for controlling side effects adds to the cost.

For the long term management of endometriosis-induced pain, no safe, alternative medical regimen with minimal side effects exists for effective suppression of pain symptoms. Many of these women choose repeated surgeries and often struggle to resist addiction to narcotic analgesics because of disabling pain. Thus, there exists a need for a safe, prophylactic method of affording patients continuing relief of pain for months and years without decrease in bone mineral density or adversely affecting fertility.

SUMMARY OF THE INVENTION

Broadly viewed, the invention provides a safe and inexpensive prophylactic treatment for endometriosis symptoms suppressed earlier by an effective therapeutic regimen that produces oligomenorrhea or amenorrhea. This prophylactic treatment is a long-term prevention of endometriosis symptoms that comprises the continuous coadministration of known steroid drug formulations to maintain the induced state of oligomenorrhea or amenorrhea in an afflicted woman. The methods and articles of manufacture of the invention provide a long term suppressive treatment that effectively manages the pain and other symptoms of endometriosis with minimal side effects, as long as the preventative method is utilized.

In one aspect of the invention, a method to prevent the recurrence of endometriosis symptoms and signs in a reproductive age woman having previously induced oligomenorrhea or amenorrhea comprises coadministering an estrogen agent with a progestin agent on a daily basis for as long as the endometriosis symptoms are desired to be prevented.

In another aspect of the invention, a method to prevent the recurrence of endometriosis symptoms and signs in a reproductive age woman comprises inducing oligomenorrhea or amenorrhea, and coadministering an estrogen agent with a progestin agent on a daily basis for as long as the symptoms are desired to be prevented.

In yet another aspect of the invention, an article of manufacture comprises the combination of (a) a composition comprising an estrogen agent with a progestin agent, and (b) printed labelling instructions associated therewith, wherein the instructions describe a method to prevent the recurrence of endometriosis symptoms and signs in a reproductive age woman having induced oligomenorrhea or amenorrhea, comprising coadministering the estrogen agent with the progestin agent on a daily basis for as long as the endometriosis symptoms are desired to be prevented.

DESCRIPTION OF SPECIFIC EMBODIMENTS

The invention provides a method for the long-term prevention with known steroid drug formulations, of the symptoms of a disease with no known cure, and with few alternative therapeutic solutions. Specifically, the invention provides methods and articles of manufacture for the prevention of endometriosis symptoms in reproductive age women. Prevention of endometriosis symptoms is achieved by continuously coadministering low doses of an estrogen agent and a progestin agent in order to maintain an induced state of temporary oligomenorrhea or amenorrhea in an afflicted woman. The methods and articles of manufacture for prophylaxis provide patients with continual pain relief over months or years without adversely affecting the bone mineral density. The methods have the added advantage of prompt restoration of fertility by stopping the administration for women desiring pregnancy.

By "endometriosis" is meant a disease in which functioning endometrial tissue is present in sites outside the uterine cavity. The disease is frequently characterized by progressive, disabling dysmenorrhea and pelvic pain around the time of the menses. While not wishing to be bound by a particular theory, it is believed that endometrial glands and stroma are shed and move retrograde through Fallopian tubes during menstruation, implanting onto the peritoneum and initiating growth. Over time, menstrual bleeding at those sites leads to angiogenesis and growth of visible lesions, pain and infertility.

By "reproductive age women" is meant women of an age between the onset of menses and menopause, typically ages about 15–45.

By "oligomenorrhea" is meant the occurrence of few episodes of vaginal bleeding in a reproductive age woman, i.e., less than about six a year.

By "amenorrhea" is meant the absence of menstrual periods, or episodes of vaginal bleeding in a reproductive age woman.

By "continuously" or "continuous" is meant on a daily basis without interruption throughout the projected monthly cycle in a reproductive age woman. For example, oral contraceptives are not administered continuously because the administration is interrupted for a period of time each month in order to permit withdrawal bleeding to occur. Continuous administration can be viewed as non-cyclic administration.

In one aspect of the invention, a method to prevent endometriosis symptoms in a reproductive age woman having induced oligomenorrhea or amenorrhea comprises coadministering an estrogen agent with a progestin agent on a daily basis for as long as the endometriosis symptoms are desired to be prevented.

In another aspect of the invention, a method to prevent endometriosis symptoms in a reproductive age woman comprises inducing oligomenorrhea or amenorrhea, and coadministering an estrogen agent with a progestin agent on a daily basis for as long as the symptoms are desired to be prevented.

By "coadministration" is meant administering a combination of therapeutic agents, such as, for example, a combination of estrogen agents and progestin agents. The combination may be administered as two separate entities or as a single combination entity.

By "estrogen agent" is meant a compound having estrogenic activity (i.e., estrusproducing), such as, for example, ethinyl estradiol, diethylstilbestrol, sterone, hydroxyestrone diacetate, mestranol, methalloenestriol, moxestrol, quinestrol, zeranal, estradiol (also referred to as 17 beta-estradiol), broparesterol, chlorotrianisene, dinoestrol, epimestrol, esterified estrogens, estropipate, conjugated equine estrogens and other compounds having estrogenic activity. Estrogen agents are well described in the art (See, for example, Martindale: *The Extra Pharmacopoeia*, 30th edition, 1993, incorporated herein by reference). Some preferred estrogen agents, and doses thereof, are provided in Table 1. A more preferred estrogen agent is ethinyl estradiol.

TABLE 1

ESTROGEN AGENTS

| TRADE NAME | Estrogen Agent | Dose | Manufacturer |
| --- | --- | --- | --- |
| ESTINYL ® | Ethinyl estradiol | 1, 2, 5, 10, 20 mcg | Lilly |
|  | Diethylstilbestrol | 1, 5 mg | Lilly |
| ESTRACE ® Cream | Estradiol | 0.1 mg | Bristol Myers Squibb |
| ESTRACE ® Tablets | Estradiol | 0.5, 1, 2 mg | Bristol Myers Squibb |
| ESTRADERM ® | Estradiol transdermal | 0.05, 0.1 mg | Ciba |
| FEMPATCH ® | Estradiol transdermal | 0.025 mg | Parke-Davis |
| ESTRATAB ® | Esterified estrogens | 0.3, 0.625, 1.25, 2.5 mg | Solvay |
| MENEST ® | Esterified estrogens | 0.3, 0.625, 1.25, 2.5 mg | Smith Kline Beecham |
| OGEN ® Cream | Estropipate | 1.5 mg | Upjohn |
| OGEN ® Tablet | Estropipate | 0.75, 1.5, 3.0 mg | Upjohn |
| ORTHO-EST ® | Estropipate | 0.75, 1.5 mg | Ortho |
| PREMARIN ® | Conjugated equine estrogens | 0.3, 0.625, 0.9, 1.25, 2.5 mg | Wyeth-Ayerst |
| VIVELLE ® | Estradiol transdermal | .0375, .05, .075, 0.1 mg | Ciba-Geigy |

By "progestin agent" is meant a compound having progestational activity (i.e., induce the formulation of a secretory endometrium), such as, for example, norethindrone (also referred to as norethisterone), ethynodiol, desogestrel, levonorgestrel, norgestrel, norgestimate, medroxyprogesterone, danazol, lynoestrenol, dydrogesterone, chlormadinone, promegesterone, gestrinone, algestone acetophenide, allyloestrenol, cyproterone acetate, demegestone, gestodene, hydroxyprogesterone hexanoate, medrogestone, megestrol, nomegestrol, ethynylnortestosterone, norpregneninolone, NSC-9564, norethynodrel, dexnorgestrel, progesterone or salts thereof, and other compounds having progestational activity. Progestin agents are well described in the art (See, for example, Martindale: *The Extra Pharmacopoeia*, 30th edition, 1993 incorporated herein by reference). Preferred salts are acetate salts. Some preferred progestin agents for effecting or maintaining temporary amenorrhea, and doses thereof, are provided in Table 2. A more preferred progestin agent is norethindrone, with norethindrone acetate being most preferred. A progestin agent is also referred to as a progestogen or a progestational hormone.

TABLE 2

PROGESTIN AGENTS

| TRADE NAME | Progestogen | mg | Manufacturer |
| --- | --- | --- | --- |
| AMEN ® | Medroxyprogesterone acetate | 10 | Carnrick |
| AYGESTIN ® | Norethindrone acetate | 5 | ESI Pharma |
| CYCRIN ® | Medroxyprogesterone | 2.5, 5, 10 | ESI Pharma |
| DANACRINE ® | Danazol* | 50, 100, 200 | Sanofi Winthrop |
| DEPO-PROVERA ® | Medroxyprogesterone acetate | 150, 400 mg/mL | Upjohn |
| MICRONOR ® | Norethindrone | 0.35 | Ortho |
| NORPLANT ® | Levonorgestrel | 30–85 mcg released daily | Wyeth-Ayerst |
| NOR-QD ® | Norethindrone | 0.35 | Searle |
| OVRETTE ® | Norgestrel | 0.075 | Wyeth-Ayerst |
| PROVERA ® | Medroxyprogesterone acetate | 2.5, 5, 10 | Upjohn |

*Progestogenic androgen, Nor-steroids are 19-Nor-androgen derivatives

The method preferably comprises the continuous administration of low-dose contraceptives after oligomenorrhea or amenorrhea has been established, wherein the low-dose contraceptives comprise both an estrogen agent and a progestin agent. By "low-dose" is meant that the estrogen agents and progestin agents are administered in a combination biologically equivalent to about 5 to about 35 micrograms of ethinyl estradiol and about 0.2 to 1.5 milligrams of norethindrone acetate, respectively, in which the weight ratio of estrogen agent to progestin agent is at least about 1:45, and more preferably at least about 1:50, calculated as ethinyl estradiol to norethindrone acetate.

By "biologically equivalent" is meant the dose of an estrogen agent having the same biological activity as about 5 to about 35 micrograms of ethinyl estradiol administered orally and the dose of a progestin agent having the same biological activity as about 0.2 to about 1.5 milligrams of norethindrone acetate administered orally. The biological activity of a compound depends on a variety of parameters, such as, for example, absorption, half-life, receptor affinity, solubility, and other physical parameters. If a first compound has a greater biological activity than a second compound, then a greater dose of the second compound would be required to achieve a dose biologically equivalent to that of the first compound. The potency of other estrogen agents varies compared to that of ethinyl estradiol. For example, about 30 micrograms of ethinyl estradiol is biologically equivalent to about 60 micrograms of mestranol or about 2,000 micrograms of estradiol. Similarly, the potency of other progestin agents varies compared to that of norethindrone acetate. For example, about 0.7 milligrams of norethindrone acetate is biologically equivalent to about 0.2 milligram of levonorgestrel. The correlations in potency between the various progestin agents and estrogen agents is known in the art (U.S. Pat. No. 5,552,394 which is incorporated herein by reference).

Preferably the continuous coadministration of a progestin agent and an estrogen agent begins within one year of the induction of oligomenorrhea or amenorrhea, more preferably before the normal menstrual cycle reasserts itself, and most preferably immediately following the induction of oligomenorrhea or amenorrhea, and can be coadministered for an indefinite period of time. The maximal permissible delay between the time of induction of oligomenorrhea or amenorrhea and the commencement of coadministration of a progestin agent and an estrogen agent depends on a number of factors including the method used for inducing oligomenorrhea and amenorrhea. For example, a longer delay may be permissible when oligomenorrhea or amenorrhea is induced surgically than when induced by other methods because the endometrium is mostly or completely destroyed. Since the endometrium has been destroyed, the endometrial lesions would not be continually fed with new retrograde transmissions of tissue.

When oligomenorrhea or amenorrhea has been induced by GnRH-agonist therapy, the maximal permissible delay is shorter and further depends on how the GnRH-agonist is administered. One of ordinary skill in the art would know how to determine when to begin the prophylactic regimen. For example, it is known in the art that about 80% of women treated by nasal administration of a GnRH agonist start bleeding after about six weeks. These women have sufficient estrogen function to build the uterine lining about two weeks prior to the onset of bleeding. One of ordinary skill in the art would use this knowledge to determine when to begin the prophylactic regimen. Preferably, the coadministration of the progestin agent and estrogen agent begins within one month of cessation of the inducement of oligomenorrhea or amenorrhea, and can be coadministered for an indefinite period of time.

Such administration can be monophasic, biphasic, or triphasic. Preferably, the administration is monophasic. By "monophasic" is meant the continuous use of one particular dose of each active agent. By "biphasic" is meant that a first dose is administered daily during a first portion of the projected monthly cycle, with a second dosing being administered daily during a second portion of the projected monthly cycle. By "triphasic" is meant that a first dose, second dose, and third dose are administered daily during a first portion, second portion, and third portion of the projected monthly cycle, respectively. Biphasic and triphasic administrations are less preferred because of the likelihood of breakthrough bleeding and the greater complexity of the regimen.

The most common symptoms and signs of endometriosis include dysmenorrhea, dyspareunia, pain unrelated to menses, discomfort upon pelvic exam, induration, and cul de sac tenderness. By "dysmenorrhea" is meant painful or difficult menstruation. By "dyspareunia" is meant the occurrence of pain during sexual intercourse. By "induration" is meant the swelling of uterine tissues due to an accumulation of endometrial lesions, blood and inflammation. By monitoring these signs and symptoms, one can determine whether they are being reduced or eliminated in a woman who is afflicted with or inclined towards the condition. The symptoms and signs of endometriosis can be quantitated in a number of ways known in the art, one of which is described further in Example 1.

Oligomenorrhea or amenorrhea can be induced in a number of ways including naturally by pregnancy, by administering an effective amount of natural or synthetic reproductive hormones, and by surgical procedures of the uterus producing permanent amenorrhea. Such hormones include gonadotropin releasing-hormone agonists (GnRH-agonists), antagonists (GnRH-antagonists), and antiestrogens, or combinations thereof. Such hormones are (See, for example, Martindale: *The Extra Pharmacopoeia*, 30th edition, 1993 incorporated herein by reference). Preferably, oligomenorrhea or amenorrhea is induced by administering a GnRH-agonist, which causes the uterine lining to become atrophic and in a state unconducife for bleeding. GnRH-agonists stimulate the gonadotropin receptors in the pituitary gland, resulting in a down-regulation of those receptors. The cessation of menstrual bleeding that develops in 80–90 percent of patients as an effect of the GnRH-agonist is maintained by the steroid treatment. In 80%–90% of women, the accelerating side-effects of hypoestrogenism (vasomotor symptoms, headache, etc.) produced by the agonist are promptly suppressed, and the relief from endometriosis-induced pain continues as long as the steroid treatment is administered.

Some preferred GnRH-agonists for effecting temporary oligomenorrhea or amenorrhea are provided in Table 3. Preferred GnRH-agonists include leuprolide acetate, nafarelin acetate, goserelin acetate, buserelin acetate, lutrelin, triptorelin (also referred to as decapeptyl), histerelin acetate, and other GnRH-agonists. Others will be apparent to those of skill in the art.

Preferably amenorrhea or oligomenorrhea is induced by administering effective amounts of a GnRH-agonist for a period of time sufficient to induce the desired state. The dose and duration is well-established in the art. Generally, the GnRH-agonist is administered for no more than about six months to reduce the risk of loss of bone density, and preferably is administered for about three months to induce the desired amenorrhea or oligomenorrhea. Effective dosing regimens for the administration of some GnRH-agonists are provided in Henzl et al. for the Nafarelin group, Administration of Nasal Nafarelin as Compared with Oral Danazol for Endometriosis-a Multi-Center, Double-Blind, Comparative Clinical Trial, *N. Eng. J. Med.* 318: 385–9 (1988); The Nafarelin European Endometriosis Trial Group, Nafarelin for Endometriosis: a Large-scale, danazol-controlled Trial of Efficacy and Safety, with 1-year Follow-up, *Fertil. Steril.* 57: 514–22 (1992); Hornstein et al., A Randomized, Double-blind Trial of 3 versus 6 Months of Nafarelin Therapy for Endometriosis-associated Pelvic Pain, Fertility and Sterility, 63: 955–62 (1995); Hornstein et al., Retreatment with Nafarelin for Recurrent Endometriosis Symptoms: Efficacy, Safety, and Bone Density, *Fertility and Sterility* 67: 1013–8 (1997); Wright et al, Short-term Lupron or Danazol Therapy for Pelvic Endometriosis, *Fertil. Steril.* 63: 504–7 (1995); Waller et al., Gonadotropin-Releasing Hormone Analogues for the Treatment of Endometriosis: Long-term Follow-up, *Fertility and Sterility* 59: 511–515 (1993); Bulletti et al., The Efficacy of Drugs in the Management of Endometriosis, *The Journal of the American Association of Gynecologic Laparoscopists* 3: 495–501 (1996); Erickson et al., GnRH Analogues in the Treatment of Endometriosis, *Endometriosis* 16: 123–145; *Physicians' Desk Reference*, 49 Edition, 1995, Medical Economics; Lindsay et al.; Regidor et al., Long-term Follow-up (up to 98 months) of 42 Patients Treated for Endometriosis with the GnRH-agonist Buserelin Acetate: Recurrence of Pain Symptoms and Pregnancy Outcome, *Eur. J. Obstet. Gynecol. Reprod. Biol.* 73: 153–60 (1997); and Shaw, R W, An open randomized comparative study of the effect of goserelin depot and danazol in the treatment of endometriosis. Zolodex Endometriosis Study Team, *Fertility and Sterility* 58: 265–272 (1992). The GnRH-agonists typically are administered by injection of a controlled release formulation designed to provide a relatively uniform release of the active agent over the desired period of time or by daily intranasal administration. See, for example, the labelling for LUPRON®.

TABLE 3

GNRH-AGONISTS

| TRADE NAME | GnRH-agonist | Dose | Manufacturer |
|---|---|---|---|
| LUPRON ® | Leuprolide acetate | 3.75, 7.5, 11.25, 15 mg parenteral | Tap |
| SYNAREL ® | Nafarelin acetate | 200 mcg nasal soln | Searle |
| ZOLODEX ® | Goserelin acetate | 3.6 mg | Zeneca |

GnRH-antagonists can also be used to induce oligomenorrhea or amenorrhea. GnRH-antagonists exert their effects by binding to the gonadotropin receptors in the pituitary gland and inhibiting the activity of those receptors. GnRH-antagonists include detirelix, antarelix (Nal-Glu), antide (Nal-Lys), centrorelix, azaline B, ganirelix, (Nal-Arg), MI-1544, MI-1892, and other GnRH-antagonists known in the art. Generally, a GnRH-antagonist will be administered for a period of about three months, preferably less than six months.

Oligomenorrhea or amenorrhea can also be induced by administering an effective amount of an antiestrogen for a period of time sufficient to induce the desired state. Antiestrogens include raloxifene acetate, tamoxifen acetate, clomiphene citrate, ICI 164384, 182,780, toremifene, droloxifene, idoxifene, keoxifene, DP-TAT-59, ethylnorgestrienone and other antiestrogens known in the art. The dose and time is well established in the art. The time for administration will be about six months to about twelve months, preferably about six months. Some preferred antiestrogens for effecting temporary oligomenorrhea or amenorrhea are provided in Table 4. More preferred antiestrogens include tamoxifen acetate, raloxifene acetate, and ethylnorgestrienone. The antiestrogens can be administered orally, by injection, and vaginally.

TABLE 4

ANTIESTROGEN

| TRADE NAME | Antiestrogen | Dose | Manufacturer |
|---|---|---|---|
| NOLVADEX ® | Tamoxifen acetate | 10 mg | Zeneca |
| EVISTA ® | Raloxifene acetate | 60 mg | Eli Lilly |
| NEMESTRAN ® | Ethylnorgistrienone | 2.5 mg twice weekly or 1.25 mg daily | |

Surgical methods are also preferred because such methods destroy the uterine lining, the endometrium. Preferred surgical procedures for effecting permanent amenorrhea include endometrial ablation procedures by electrocautery (surface or needle) methods, thermal (balloon or needle) methods, laser methods, or electromagnetic methods. Other applicable surgical procedures include radio-surgery, circulatory embolization, and hysterectomy (partial or complete) by laparoscopy or open surgery. (Wheeler et al.; Sutton et al., Prospective, Randomized, double-blind, Controlled Trial of Laser Laparoscopy in the Treatment of Pelvic Pain Associated with Minimal, Mild, and Moderate Endometriosis, *Fertility and Sterility* 62: 696–700 (1994); Palter et al., Office Microlaparoscopy Under Local Anesthesia for Chronic Pelvic Pain, *J. Am. Assoc. Gynecol. Laparos.* 3:359–364 (1996); Faber et al., Microlaparoscopy: a Comparative Study of Diagnostic Accuracy, *Fertility and Sterility* 67: 952–54 (1997); Fisbume, Office Laparoscopy sterilization with Local Anesthesia, *J. Reprod. Med.* 18:233–4 (1977); Casey, Laparoscopy Under Local Anesthesia, *JR Soc. Med.* 77: 985–6 (1984); Milki et al., Office laparoscopy Under Local Anesthesia for Gamete Intrafallopian Transfer: Technique and Tolerance, *Fertility and Sterility* 68: 128–32 (1997); Vilos et al., Endometrial ablation with a thermal balloon for the treatment of menorrhagia, *The Journal of the American Association of Gynecologic Laparoscopists* 3: 383–387 (1996); Soderstrom et al., Endometrial ablation using a distensible multielectrode balloon, *The Journal of the American Association of Gynecologic Laparoscopists* 3: 403–407 (1996); Candiani et al, Repetitive conservative surgery for recurrence of endometriosis, *Obstet Gynecol* 77: 421–424 (1991)).

Oral contraceptives can be used to induce oligomenorrhea and amenorrhea, but this method is less preferred since the uterine lining remains ripe for bleeding, which usually resumes despite continued administration of the oral contraceptives.

In a preferred embodiment, endometriosis symptoms are prevented by continuously coadministering ethinyl estradiol and a progestin agent on a daily basis. Trade names of ethinylestradiol-containing oral contraceptive include ADEPAL®, ANACYCLIN®, ANOVLAR®, BINORDIOL®, BINOVUM®, BIPHASIL®, BIVLAR®, BREVICON®, BREVINOR®, CILEST®, CONCEPLAN®, CONOVA®, CYCLOSA®, DEMULEN®, DESOLETT®, DIANE®, DIANETTE®, DUOLUTON®, EDIWAL®, EGOGYN®, ESTRO-PRIMOLUT®, ETALONTIN®, EUGYNON®, EVANDOR-D®, GINODEN®, FEMOVAN®, FOLLIMIN®, FEMODENE®, FOLLINETT®, FYSIOQUENS®, GYNERA®, GYNOPHASE®, LEVLEN®, GYNOVLANE®, LOESTRIN®, GYNOVLAR®, LOGYNON®, LO/OVRAL®, LYNDIOL®, LUTESTRAL®, MARVELON®, LYNDIOLETTE®, MENOVA®, LYN-RATIOPHARM MENOFLUSH-MENOGLOED®, MICRODIOL®, MILVANE®, MICROGYNON®, MIXOGEN®, MILLI ANOVLAR®, MINILYN®, MINESTRIN®, MINIDRIL®, MINIPREGNON®, MINISTAT®, MINIPHASE®, MINOVLAR®, MINOVRAL®, MINULET®, MINULETTE®, MODICON®, NEO-EUNOMINE®, NELOVA®, NEOCON®, NEO LYNDIOL®, NEO-EUNOMIN®, NEOGYNON®, NEOMENS®, NEOGYNONA®, NEORLEST®, NORDETTE®, NEOSTEDRIL®, NEOVLETTA®, NORCEPT-E®, NORCYCLIN®, NORDETTE®, NORDIOL®, NORETHIN®, NORIMIN®, NORINYL®, NOELESTRIN®, NOVOGYN®, NORMAPAUSE®, NORMAPHASIC®, NORMOVLAR ED®, NORQUENTIEL®, NURIPHASIC®, OLOGYN®, OSTROPRIMOLUT®, ORLEST®, OESTRO-GYNAEDRON®, ORTHO® (VARIOUS), ORTHOCYCLEN®, ORTHONETT NOVUM®, ORTHONOVUM® (VARIOUS), OVAMEZZO®, OVANON®, OVARIOSTAT®, OVCON®, OVIDOL®, OVAPLEX®, OVRESTA®, OVOSTAT®, OVOWOP®, OVRAL®, OVRAN®, OVRANETTE®, OVRANET®, OVULEN®, OVYSMEN®, PAUSERIL®, PERIKURSAL®, PHAEVA®, PHASICON®, PHYSIOSTAT®, PLANOR®, PLANUM®, POLY-GYNAEDRON®, PRACTIL®, PREGNON®, PRIMOSISTON®, PROGYLUT®, PROLORFIN®, PROSISTON®, REGUNON®, RESTOVAR®, SECURGIN®, SEQUILAR®, SEQUILARUM®, SINOVULA®, STEDIRIL®, SYNFASE®, SYNPHASE®, SYNPHASIC®, TETRAGYNON®, TRIADENE®, TRENTOVLANE®, TRIELLA®, TRIAGYNON®, TRICILOR®, TRI-LEVLEN®, TRIONETTA®, TRIMENULET®, TRINORDIOL®, TRINOVUM®, TRI-NORINYL®, TRINOVUM®, TRISTEP®, TRIPHASIL®, TRIQUILAR®, VARNOLINE®, AND YERMONIL®. Some preferred monophasic ethinyl estradiol/progestin formulations for effecting or maintaining temporary amenorrhea, and doses thereof, are provided in Table 5. More preferably, the progestin is norethindrone or its acetate salt. Preferably, about 5 to about 35 micrograms of ethinyl estradiol and about 0.2 to about 1.5 milligrams of norethindrone or its acetate are continuously coadministered. Most preferably, the progestin is norethindrone acetate and the weight ratio of the ethinyl estradiol to norethindrone acetate is at least about 1:45. By at least about "1:45" is mean that the weight of norethindrone acetate administered is at least 45 times greater than the weight of ethinyl estradiol administered. Most preferred is the continuous coadministration of about 20 micrograms of ethinyl estradiol and about 1.0 milligrams of norethindrone acetate.

This lower "micro dose" formulation with 20 micrograms of ethinyl estradiol and 1.0 milligram norethindrone acetate has been prepared for cyclic administration, but has not been widely accepted by women for contraception because of increased breakthrough bleeding during the early months of such cyclic use (Hawkins et al:), and because of less effective contraceptive protection than other so called "low-dose" formulations containing more estrogen, typically 30 or 35 micrograms. Applicant has determined that this formulation is surprisingly efficacious for satisfactorily maintaining the suppression of the ovarian cycles and amenorrhea induced by GnRH-agonists in reproductive age women with endometriosis.

TABLE 5

ORAL ETHINYL ESTRADIOL/PROGESTIN FORMULATIONS

| TRADE NAME | Progestin | mg | mcg EE | Mfgr. |
| --- | --- | --- | --- | --- |
| ALESSE ® | Norethindrone acetate | 1.0 | 20 | American Home Products |
| BREVICON ® 21 Day | Norethindrone | 0.5 | 35 | Searle |

TABLE 5-continued

ORAL ETHINYL ESTRADIOL/PROGESTIN FORMULATIONS

| TRADE NAME | Progestin | mg | mcg EE | Mfgr. |
| --- | --- | --- | --- | --- |
| DEMULEN ® 1/35-21 | Ethynodiol diacetate | 1.0 | 35 | Searle |
| DESOGEN ® | Desogestrel | 0.15 | 30 | Organon |
| LEVLEN ® -21 | Levonorgestrel | 0.15 | 30 | Berlex |
| LOESTRIN ® 1/20 | Norethindrone acetate | 1.0 | 20 | Parke-Davis |
| LOESTRIN ® 1.5/30 | Norethindrone acetate | 1.5 | 30 | Parke-Davis |
| LO/OVRAL ® | Norgestrel | 0.3 | 30 | Wyeth-Ayerst |
| MODICON ® | Norethindrone | 0.5 | 35 | Ortho |
| NELOVA ® 0.5/35 | Norethindrone | 0.5 | 35 | Warner Chilcott |
| NORDETTE ® -21 | Levonorgestrel | 0.15 | 30 | Wyeth-Ayerst |
| NORINYL ® 1 + 35 21 Day | Norethindrone | 1.0 | 35 | Searle |
| ORTHO-CEPT ® | Desogestrel | 0.15 | 30 | Ortho |
| ORTHO-CYCLEN ® | Norgestiniate | 0.250 | 35 | Ortho |
| ORTHO-NOVUM ® | Norethindrone | 1.0 | 35 | Ortho |
| OVCON ® 35-21 | Norethindrone | 0.4 | 35 | Bristol-Myers Squibb |

The safety of this regimen has been established by many placebo-controlled clinical trials that have evaluated efficacy and safety prior to FDA approval of these drugs for contraception (Pincus et al., Effects of Certain 19-Nor-Steroids Upon Reproductive Processes, *Ann. of New York Acad. of Sci.* 71:677–90 (1958); Pasquale, S. A., Clinical Results with a new low-dose oral contraceptive utilizing norethindrone/estinyl estradiol, *Contraception* 12:495–503 (1975); Bounds et al., A Randomized double-blind trial of two low dose combined oral contraceptives, *Br. J. Obstet. Gynecol.* 86:325–29 (1979)) and in recently reported, clinical trials of postmenopausal replacement therapy (Williams et al., A Study of Combined Continuous Ethinyl Estradiol and Norethindrone Acetate for Postmenopausal Hormone Replacement, *Am. J. Obstet. Gynecol.* 162: 438–46 (1990); Speroff et al., The Comparative Effect on Bone Density, Endometrium, and Lipids of Continuous Hormones as Replacement Therapy (CHART Study), A Randomized Controlled Trial, *JAMA* 276: 1397–1403 (1996)). Cardiovascular events such as heart attacks and strokes, breast cancer, and adverse lipid and carbohydrate metabolic consequences have been established to be dose-related, but are either not evident, or are insignificant with the 35 microgram dose in non-smoking women. Continuous regimen with norethindrone, 0.5 milligram, and other synthetic progestins alone, have received FDA approval for contraception, but their efficacy is low and breakthrough bleeding common. (Hawkins, et al., A comparative study of three low dose progestogens, chlormadinone acetate, megestrol acetate, and norethindrone, as oral contraceptives, *Br. J. Obstet. Gynecol.* 84: 703–13 (1977); Stadberg et al., 17 beta-estradiol and norethisterone acetate in low doses as continuous combined hormone replacement therapy, *Maturitas* 23: 31–39 (1996); Plunkett et al., Prolonged effects of a novel, low-dosage continuous progestin-cyclic estrogen replacement program in postmenopausal women, *Am. J. Obstet. and Gynecol.* 166: 117–121 (1992)).

A sentinel study reported in 1990 the use of several steroid combinations taken continuously by postmenopausal women for two years (Williams et al.), showed only a 10 percent frequency of breakthrough bleeding, and a beneficial increase in bone mineral density during therapy. In further placebo-controlled trials conducted with large numbers of subjects, and different absolute amounts and various estrogen/progestogen ratios, no adverse effects were observed on bleeding and lipid metabolism, and benefit for bone was unmistakable (Speroff et al.). The protective effect of progestins on the endometrium was confirmed. These reassuring data suggest that various formulations of about 5 to about 20 micrograms of ethinyl estradiol with about 0.5 to about 1.0 milligram of norethindrone acetate are safe, elective therapies for long-term use.

The decades-long concern about oral contraceptives as cancer promoters in the endometrium has been satisfied conclusively. Experience and data from young women using estrogen-progestin combination drugs cyclically for contraception indicate a protective effect of progestin on the endometrium when included with the estrogen component (Bounds et al.). Only when the progestin is given cyclically is the protective effect lost. Similarly, observations of the 1970's showed unmistakably that unopposed estrogen given to postmenopausal women had a dose-related effect producing significant pre-malignant lesions and carcinogenesis of the endometrium. Thereafter, the safety of estrogen therapy was secured through the addition of cyclic progestin during at least 12 days per cycle. Recently, large clinical trials (e.g., PEPI) have demonstrated that continuous estrogen-progestin therapy in standard doses, taken daily for at least three years during the postmenopausal time, is associated with no increased risk of precancerous lesions or carcinogenesis of the endometrium (The Writing Group for the PEPI Trial, Effects of Estrogen or Estrogen/Progestin Regimens on Heart Disease Risk Factors in Postmenopausal Women, *JAMA* 273: 199–208 (1996)). These data from tens of thousands of young women and older women taking estrogen-progestin therapy either cyclically or continuously for different indications, reassure physicians and patients alike that progestins counteract the growth-promoting action of estrogen on the endometrium.

The progestin agent and estrogen agent can be coadministered as a single dosage form or as multiple dosage forms. The agents can be administered orally, by injection, nasally, transdermally (for example, by patch or vaginal cream), or by implant in an appropriate controlled release composition. Oral administration can be achieved by tablet or capsule. Formulations and dosing regimens for such tablets or capsules are well known in the art for the administration of oral contraceptives or for hormone replacement therapy (Pasquale; Bounds et al.; Williams et al.; Hawkins et al.; The Writing Group for the PEPI Trial; U.S. Pat. Nos. 5,552,394, 5,591,753, 5,646,137; *Physicians' Desk Reference*, 49 Edition, 1995, Medical Economics; Munk-Jensen et al., *Am.*

J. Obstet. and Gynecol. 171:132–138 (1994); Speroff et al.; Johannisson et al., Int. J. Fertil Womens Med (1997) 42 Supp 2:388–398; Rozenberg et al., Int. J. Fertil Womens Med (1997) 42 Supp 2:376–387; Sitruk-Ware et al., J. Steroid Biochem Mol Bio (1995) 53(1–6):247–251; Oosterbaan et al., Maturitas (1995) 21:211–219). Transderma administration is also well known in the art and is described in U.S. Pat. No. 4,906,169, which is incorporated herein by reference. The progestin agent and estrogen agent can be administered by the same method or by different methods. For example, an estrogen agent can be administered orally while a progestin agent is administered by implant or by injection. Alternatively, for example, an estrogen agent can be administered transdermally, vaginally, or by implant while a progestin agent is administered orally, by implant, or by injection. Preferably, however, the agents are coadministered orally as a single dosage unit, such as a monophasic pill or capsule.

In yet another aspect of the invention, an article of manufacture comprises the combination of (a) a pharmaceutical composition comprising an estrogen agent with a progestin agent, and (b) printed labelling instructions associated therewith, wherein the instructions describe a method to prevent endometriosis symptoms in a reproductive age woman having induced oligomenorrhea or amenorrhea, comprising coadministering the estrogen agent with the progestin agent on a daily basis for as long as the endometriosis symptoms are desired to be prevented. The composition comprises a pharmaceutically acceptable excipient and a therapeutically effective amount of an estrogen agent and a progestin agent as defined hereinbefore. The labelling instructions provide for administering a sufficient amount of the estrogen agent and progestin to a reproductive age woman to prevent symptoms of endometriosis. Printed labelling instructions are functionally related to a composition comprising a progestin agent with an estrogen agent inasmuch as such labelling instructions describe a method to prevent endometriosis symptoms comprising administering the composition. While a progestin/estrogen composition has been used as a contraceptive, the combination of such a composition with labelling instructions describing the use of the composition to prevent endometriosis symptoms was lacking in the art prior to the applicant's invention. The labelling instructions are key to this aspect of the invention in that before a compound can be approved for any particular use, it must be approved for marketing by the United States Food and Drug Administration. Part of that process includes providing a label that will accompany the pharmaceutical composition which is ultimately sold. While the label will include a definition of the composition and such other items such as the clinical pharmacology, mechanism of action, drug resistance, pharmacokinetics, absorption, bioavailability, contraindications and the like, it will also provide the necessary dosage, administration and usage. Thus, the combination of the drug with appropriate labelling instructions is important for the proper usage of the drug once it gets on the market. Such labelling instructions will describe the usage in accordance with the method set forth hereinbefore.

EXAMPLES

Example 1

Figure 1A:
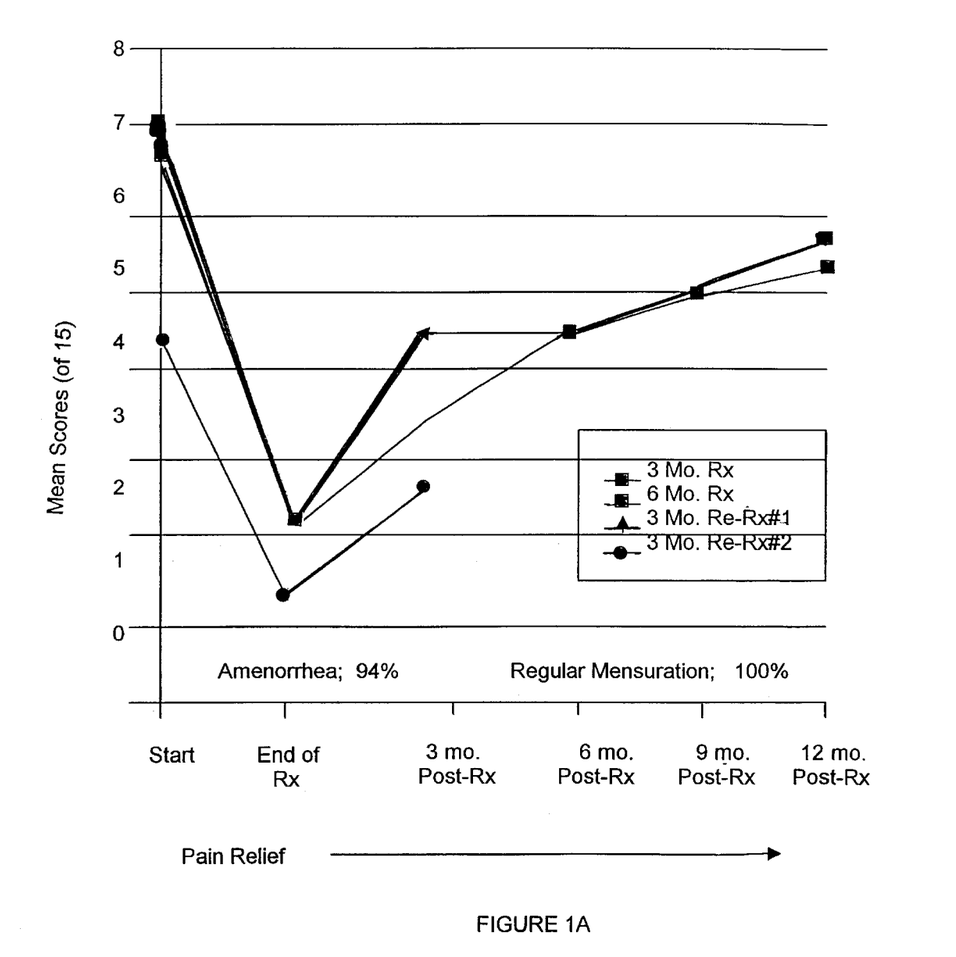
FIG. 1A is a graph showing the effect of Nafarelin on symptoms and signs of endometriosis during and after a three-month treatment, six-month treatment, and three-month re-treatment.

Maintenance of Oligomenorrhea or Amenorrhea by the Continuous Administration of LOESTRIN® 1/20 Continuously Following a Three Month Administration of a GnRH-agonist Oligomenorrhea or amenorrhea is induced in women enrolled in the study by intranasally administering 200 mg nafarelin acetate, a GnRH-agonist, twice per day for three months. Data in FIG. 1A are from women followed for 3 to 12 months following completion of nafarelin therapy. 419 patients are participating in four different clinical trials: ICM 1067, Lab/Naf 25, Naf 001, and Lab/Naf 31, which compare the results of three vs six months of therapy. 57 patients are participating in two clinical trials, Naf 601 (labeled Re-Rx#1) and Naf 1476 (labeled Re-Rx2), which compare postoperative treatment or recurrent regimen. Symptoms and signs of endometriosis are monitored for up to twelve months. Pain scores are determined as follows. The patients evaluate their own dysmenorrhea, dyspareunia, and pain unrelated to menses on a scale of 0 to 3 (absent, mild, moderate, and severe). In addition, the investigators use the same scale for induration and tenderness. The patients' and investigators' ratings are combined to yield a profile of symptoms and signs: none (0), mild (1 to 2), moderate (3 to 5), severe (6 to 10), and very severe (11 to 15). Thus, the maximal score is 15. Pain is relieved initially, but recurrence of symptoms/signs follows as menstruation is restored during observation.

Figure 1B:
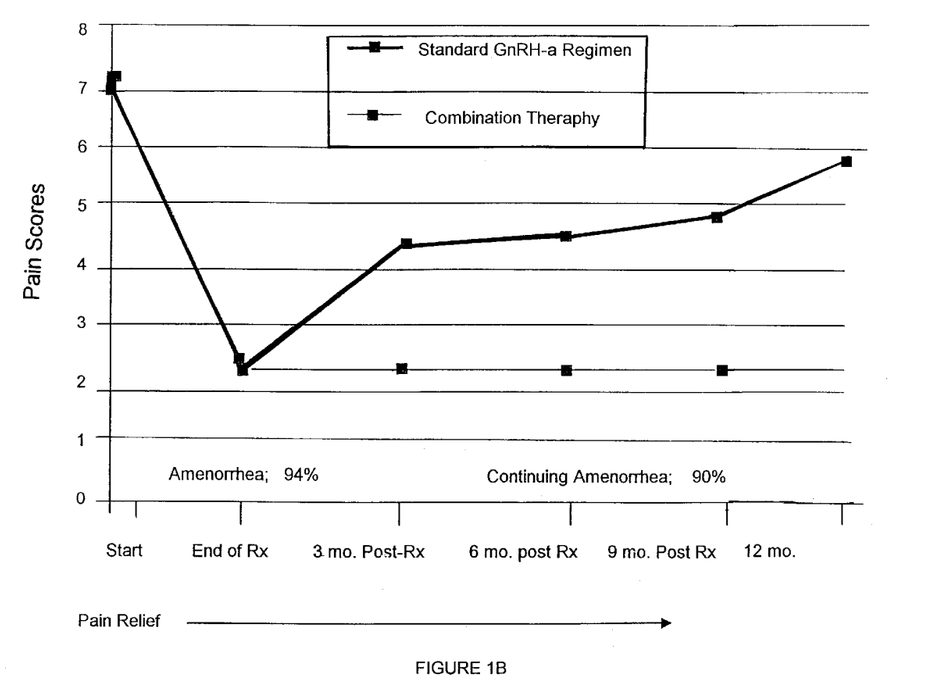
FIG. 1B is a graph showing the effect of combination therapy for long-term suppression of pain from endometriosis. The combination therapy consists of a three-month treatment with GnRH-agonist, followed by continuous preventative therapy with a low-dose estrogen agent and progestin agent.

The results shown in FIG. 1B compare the symptoms and signs of endometriosis occurring in women untreated after cessation of GnRH-agonist therapy alone to those of fifteen women treated with oral contraceptives following the cessation of GnRH-agonist therapy. Immediately after ceasing the GnRH-agonist therapy, or prior to the initial post-therapy mensus, LOESTRIN® 1/20 (comprising 1 milligram norethindrone acetate and 20 micrograms ethinyl estradiol per tablet) is administered continuously. Administration of Loestrin following cessation of GnRH-agonist therapy continued to suppress the symptoms and signs of endometriosis for the duration of the study.

Example 2

Maintenance of Oligomenorrhea or Amenorrhea by the Continuous Administration of Brevicon LOOVRAL® (0.3 milligram norethindrone and 30 micrograms ethinyl estradiol per tablet) is administered daily on a continuous basis to women having induced oligomenorrhea or amenorrhea. Oligomenorrhea or amenorrhea has been induced in these women by various methods as described above. The duration of administration varies according to the individual woman's wishes. Some women wish to cease prophylactic administration in order to begin a pregnancy, some wish to cease prophylactic administration to await return of their menstrual cycles, hoping that the symptoms are reduced and that no further administration is necessary, and others wish to continue the administration indefinitely. Symptoms and signs of endometriosis are monitored over the course of the administration as for Example 1.

Example 3

Maintenance of Oligomenorrhea or Amenorrhea by the Continuous Administration of Demulen 1/35

DEMULEN® 1/35 (1.0 milligram ethynodiol diacetate and 35 micrograms ethinyl estradiol per tablet) is administered daily on a continuous basis to women having induced oligomenorrhea or amenorrhea. Oligomenorrhea or amenorrhea is induced in these women by various methods as described above. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

Example 4

Maintenance of Oligomenorrhea or Amenorrhea by the Continuous Transdermal Administration of an Estrogen Agent and a Progestin Agent from a Single Patch Estradiol and norethindrone acetate are coadministered transdermally from a single patch on a continuous basis to women having induced oligomenorthea or amenorrhea, providing a daily dose of 50 micrograms estradiol and about 250 micrograms norethindrone acetate. Oligomenorrhea or amenorrhea is induced in these women by various methods as described above. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

Example 5

Maintenance of Oligomenorrhea or Amenorrhea by the Continuous Transdermal Administration of an Estrogen Agent and a Progestin Agent from Separate Patches ESTRADERM® (estradiol) and norethindrone acetate are administered transdermally from a separate patches on a continuous basis to women having induced oligomenorrhea or amenorrhea, providing a daily dose of 0.25, 0.5, or 1.0 milligram estradiol and 0.25 milligram norethindrone acetate. Oligomenorrhea or amenorrhea is induced in these women by various methods as described above. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

Example 6

Maintenance of Oligomenorrhea or Amenorrhea by the Continuous Transdermal Administration of an Estrogen Agent coupled with the Continuous Oral Administration of a Progestin Agent VIVELLE® (estradiol) is administered transdermally and NOR-QD® (0.35 milligram norethindrone per tablet) is administered orally on a continuous basis to women having induced oligomenorrhea or amenorrhea, providing a daily dose of 0.25, 0.5, or 1.0 milligram estradiol. Oligomenorrhea or amenorrhea is induced in these women by various methods as described above. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

Example 7

Maintenance of Oligomenorrhea or Amenorrhea by the Continuous Oral Administration of an Estrogen Agent coupled with the Continuous Administration by Implant of a Progestin Agent ESTINYL® (5 micrograms ethinyl estradiol per tablet) is orally administered in addition to the continuous administration of levonorgestrel by a NORPLANT® implant in women having induced oligomenorrhea or amenorrhea, providing a daily dose of levonorgestrel of about micrograms initially, followed by a decline to about 50 micrograms by nine months and to about 35 micrograms by eighteen months with a further decline thereafter to about 30 micrograms. Oligomenorrhea or amenorrhea is induced in these women by various methods as described above. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

Example 8

Maintenance of Oligomenorrhea or Amenorrhea by Parenteral Administration of a Progestin Agent and the Continuous Transdermal Administration of an Estrogen Agent DEPO-PROVERA® (medroxyprogesterone acetate) is administered by injection at a concentration of 150 milligrams/milliliter at three month intervals and 50 micrograms ESTRADERM® (estradiol) is administered transdermally on a continuous basis to women having induced oligomenorrhea or amenorrhea. Oligomenorrhea or amenorrhea is induced in these women by various methods as described above. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

Example 9

Maintenance of Oligomenorrhea or Amenorrhea by the Continuous Administration of NORINYL® 1/35 Continuously Following Vaginal Administration of an Antiestrogen Oligomenorrhea or amenorrhea is induced in women by vaginally administering 1.25 mg of ethylnogestrienone daily for two months. Following ethylnorgestrienone treatment, NORINYL® 1/35 (comprising 1.0 milligram norethindrone and 35 micrograms ethinyl estradiol per tablet) is administered continuously for long-term prevention of endometriosis symptoms. The duration of administration varies according to the individual woman's wishes. Some women may wish to cease prophylactic administration in order to begin a pregnancy, some may wish to cease prophylactic administration to await return of their menstrual cycles, hoping that the symptoms are reduced and that no further administration is necessary, and others may wish to continue the administration indefinitely. Symptoms and signs of endometriosis are monitored over the course of the administration as for Example 1.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. A method to prevent the recurrence of endometriosis symptoms or signs in a reproductive age woman having oligomenorrhea or amenorrhea induced by administration of a gonadotropin releasing-hormone (GnRH) agonist, which method comprises continuously co-administering, following the cessation of said inducement, an estrogen agent with a progestin agent to the woman on a daily basis for a period of time sufficient to prevent the recurrence of endometriosis symptoms or signs.

2. The method of claim 1, wherein the estrogen agent is administered at a level that is biologically equivalent to about 5 to about 35 micrograms of ethinyl estradiol and the progestin agent is biologically equivalent to about 0.2 to about 1.5 milligrams of norethindrone acetate, wherein the weight ratio of said estrogen agent to said progestin agent is at least about 1:45 calculated as ethinyl estradiol to norethindrone acetate.

3. The method of claim 1, wherein the estrogen agent and the progestin agent are coadministered transdermally.

4. The method of claim 1, wherein the estrogen agent and the progestin agent are coadministered orally.

5. The method of claim 4, wherein the estrogen agent and the progestin agent are coadministered as a monophasic tablet or capsule.

6. The method of claim 5, wherein the monophasic tablet comprises about 5 to about 35 micrograms of ethinyl estradiol and about 0.2 to about 1.5 milligrams of norethindrone or norethindrone acetate.

7. The method of claim 6, wherein the monophasic tablet comprises about 20 micrograms of ethinyl estradiol and about 1.0 milligram of norethindrone acetate.

8. The method of claim 1, wherein the estrogen agent is ethinyl estradiol and the progestin agent is norethindrone acetate.

9. The method of claim 8 wherein the weight ratio of the ethinyl estradiol to norethindrone acetate is at least about 1:45.

10. The method of claim 9, wherein the weight ratio is about 1:50.

11. The method of claim 1, wherein the GnRH agonist is selected from the group consisting of nafarelin acetate, leuprolide acetate, goserelin acetate, and buserelin acetate.

12. A method to prevent the recurrence of endometriosis symptoms or signs in a reproductive age woman, which method comprises inducing oligomenorrhea or amenorrhea in the woman by administering a gonadotropin releasing-hormone (GnRH) agonist, and, following the cessation of said inducement, continuously co-administering to the woman an estrogen agent with a progestin agent on a daily basis for a period of time sufficient to prevent the recurrence of endometriosis symptoms or signs.

13. The method of claim 12, wherein the estrogen agent is administered at a level that is biologically equivalent to about 5 to about 35 micrograms of ethinyl estradiol and the progestin agent is biologically equivalent to about 0.2 to about 1.5 milligrams of norethindrone or norethindrone acetate, wherein the weight ratio of said estrogen agent to said progestin agent is at least about 1:45 calculated as ethinyl estradiol to norethindrone acetate.

14. The method of claim 12, wherein the estrogen agent and the progestin agent are coadministered transdermally.

15. The method of claim 12, wherein the estrogen agent and the progestin agent are coadministered orally.

16. The method of claim 15, wherein the estrogen agent and the progestin agent are coadministered as a monophasic tablet or capsule.

17. The method of claim 16, wherein the monophasic tablet comprises about 5 to about 35 micrograms of ethinyl estradiol and about 0.2 to about 1.5 milligrams of norethindrone or norethindrone acetate.

18. The method of claim 17, wherein the monophasic tablet comprises about 20 micrograms of ethinyl estradiol and about 1.0 milligram of norethindrone acetate.

19. The method of claim 12, wherein the estrogen agent is ethinyl estradiol and the progestin agent is norethindrone acetate.

20. The method of claim 19, wherein the weight ratio of the ethinyl estradiol to norethindrone acetate is at least about 1:45.

21. The method of claim 20, wherein the weight ratio is about 1:50.

22. The method of claim 21, wherein the GnRH-agonist is selected from the group consisting of nafarelin acetate, leuprolide acetate, goserelin acetate, and buserelin acetate.

* * * * *